United States Patent [19]

Halleck

[11] 4,382,824

[45] May 10, 1983

[54] METHOD FOR DISINFECTING AND CLEANING CONTACT LENSES

[75] Inventor: Frank E. Halleck, Erie, Pa.

[73] Assignee: American Sterilizer Company, Erie, Pa.

[21] Appl. No.: 316,937

[22] Filed: Oct. 30, 1981

Related U.S. Application Data

[63] Continuation-in-part of Ser. No. 187,760, Sep. 16, 1980, abandoned.

[51] Int. Cl.³ .............................................. B08B 3/12
[52] U.S. Cl. ......................................... 134/1; 422/20; 422/128
[58] Field of Search ....................... 134/1; 422/20, 128

[56] References Cited

U.S. PATENT DOCUMENTS 3,697,222 10/1972 Sierra .................................... 422/20
3,720,402 3/1973 Cummins et al. ...................... 134/1
4,211,744 7/1980 Boucher ................................ 422/20

FOREIGN PATENT DOCUMENTS 2438607 2/1975 Fed. Rep. of Germany ........ 422/20

Primary Examiner—Ferris H. Lander
Attorney, Agent, or Firm—Robert D. Yeager

[57] ABSTRACT

A process is described for cleaning and disinfecting a soiled contact lens in a single unit operation. The soiled contact lens is immersed in a cavitation-supporting saline solution which is at ambient temperature. The lens is then subjected to ultrasonic energy which is transmitted through the solution at a frequency of between 62 and 72 kHz and an intensity of between 0.8 and 2.0 watts per ml. of solution. This procedure causes substantially all of the soil to dislodge from the lens before the combined elapsed time and temperature conditions within the solution produce any substantial protein denaturation on the lens. Ultrasonic energy is transmitted continuously through the solution at the same frequency and intensity ranges so that the temperature of the solution does not exceed about 65° C. but the total elapsed period of the ultrasonic energy transmission, not to exceed about 20 minutes, must be sufficient to effect the disinfection of the lens.

2 Claims, 3 Drawing Figures

METHOD FOR DISINFECTING AND CLEANING CONTACT LENSES

CROSS REFERENCE TO RELATED APPLICATION

This application is a continuation-in-part of applicant's prior copending application, Ser. No. 187,760, filed Sept. 16, 1980 now abandoned.

BACKGROUND OF THE INVENTION

1. Field of the Invention

This invention relates to a method for cleaning and disinfecting optical contact lenses by the application of ultrasonic energy.

2. Description of the Prior Art

Optical contact lenses enjoy increasing popularity among persons requiring vision correction. The first contact lenses were made of glass; later plastics, principally polymeric methacrylates, replaced glass as the material for forming so-called "hard" contact lenses. More recently, hydrophilic copolymers have been used to produce so-called "soft" contact lenses.

A contact lens rests on the surface of the cornea, which is covered with a natural fluid layer of tears, oil and other glandular secretions that constantly bathe and moisten the eye. It is important, therefore, that contact lenses be kept free of bacteria and soil that may be harmful to the eye tissue.

Elaborate procedures, often involving the use of expensive equipment and chemicals, have been devised to enable the user of contact lenses to disinfect and/or clean the lenses on a daily basis in order to prevent damage to or infection of the eye. The term "disinfect" or "disinfection" as used herein means to destroy pathogens (or disease-carrying organisms). The term "clean" or "cleaning" as used herein means the removal of separable foreign matter such as dirt, dust and particularly secretions from the eye including the protein lysozyme. While there is no specific requirement to disinfect hard contact lenses, disinfection has been found to be highly desirable.

Because of their hydrophilic properties, soft contact lenses pose a considerable challenge to disinfection. Disinfection of soft contact lens material was first carried out by placing the lenses into a container which was then placed in a boiling water bath for 10 or 15 minutes. The unit devised for this procedure was essentially a double boiler. Continued boiling at 100° C. had a tendency to cause the lens material to degrade; more importantly, however, the high temperature caused the protein material present on the surface of the lens to denature and become "baked" on the lens surface.

Thereafter, chemical disinfection systems were devised to replace the heating units; these systems required at least two and sometimes three separate solutions to accomplish disinfection, but enjoyed some early acceptance because of their convenience over the use of heating units. The incidence of "red eye," a condition of eye irritation that may be caused by preservatives present in the solutions, prompted many soft contact lens uses to revert to heat disinfection systems.

The next improvement in contact lens disinfection was the development of a dry heater wherein the heat source was a dry heat source, essentially a metal plate with a resistance heater. However, the temperature of the plate was difficult to control; therefore, there was still presented a danger of overheating the lens and baking protein onto the surface of the lens. Rather than using a metal plate, some units contained paraffin which surrounded the cavity in which the lens case was placed. The paraffin was heated to a liquid state. Because paraffin has a lower specific heat than metal, the paraffin retained heat at a more uniform level than the metal. The lens deterioration problem was alleviated, but the protein denaturation and baking problems remained.

All of the units which disinfect contact lenses by heating them are required, by present government regulation, to maintain the lenses in an environment having a minimum temperature of 80° C. for a minimum time period of ten minutes. Most units include a safety factor so that in reality the temperature reaches 90° C. or even 100° C. for at least a portion of that time period. At these temperatures any protein which remains on the surface of the lens will denature and be baked on.

Throughout the evolution of disinfection techniques for soft contact lenses, the almost universal technique for cleaning the lenses was a manual one, in which the user applied a cleaning solution to each lens and rubbed it between his fingers. This practice, carried out either before or after the separate disinfection step, physically removed soil and debris from the lens. The same manual cleaning procedure long has been used with hard contact lenses. The problem in using the manual cleaning procedure for soft contact lenses is that the lens is likely to tear or be otherwise damaged if the lens is rubbed vigorously enough to remove all of the protein. But, if the lens is not rubbed vigorously enough, some of the protein remains on the lens and is denatured and baked on when the lens is placed in a heating unit for disinfection. One type of chemical cleaning system involved the uses of enzymes. The purpose of the enzymes was to remove the protein from the surface of the lens by breaking it down. However, once protein build up occurred on the surface of the lens, the enzymes were largely ineffective.

Ultrasonic cleaning techniques were developed in response to the problems associated with the aforementioned cleaning procedures. In this way the lens can be cleaned without the chance of damaging the lens. Ultrasonic cleaning techniques generally involve placing the contact lenses into a holder and immersing the holder in a cleaning fluid bath. The holder is adapted so that the cleaning fluid can circulate around the lenses. The ultrasonic energy causes a phenomenon known as cavitation to occur which cleans the foreign matter from the surface of the lenses.

Cavitation occurs in liquids exposed to periodic oscillatory forces and is usually explained as the formation and rapid collapse of small cavities in the liquid. The collapse of these cavities produces large amplitude shock waves and elevated local temperatures. Electrical discharges are also believed to occur during the collapsing phase. For further discussion of cavitation in liquids produced by ultrasonic energy, see e.g. U.S. Pat. Nos. 3,837,805; 3,481,687; and 4,086,057; and "Ultrasonics" by R. M. G. Boucher, Canadian Journal of Pharmaceutical Sciences, Vol. 14, No. 1, 1979, pp. 1–12.

In the known applications of ultrasonic energy to contact lens cleaning and disinfection, the cleaning bath is heated prior to introducing the lenses into the bath. Generally, the cleaning bath is maintained at a temperature of at least 65° C. throughout the cleaning and disinfection processes. Thus the same problems of protein denaturation and degradation of the lens material occur as in other thermal disinfection units due to the use of such a high temperature. However, a synergistic effect between the ultrasonic energy and the temperature of the cleaning bath is observed so that disinfection does occur in the cleaning bath at temperatures lower than the temperatures which would be required without the application of the ultrasonic energy to the cleaning bath. For further discussion of the synergistic effect between the temperature of the bath and the application of ultrasonic energy to the bath, see U.S. Pat. Nos. 3,837,805 and 4,211,744.

West German patent application No. 24 38 067 describes an ultrasonic cleaning and disinfection unit for contact lenses in which the lenses are cleaned and disinfected at a temperature below 70° C. and preferably below 55° C. Ultrasonic energy is transmitted through a biologically inert, nonlethal solution containing the lenses at a frequency of 55 kHz at a power level of between 3 and 5 watts. A time period of between 1½ and 4 hours is required before the lenses are disinfected, thus the procedure is impractical when a short cleaning and disinfection period is required. The unit contains temperature control means to shut off the source of ultrasonic energy when the temperature rises more than a few degrees above the desired level and reactivates the source of ultrasonic energy when the temperature falls more than a few degrees below the desired level.

SUMMARY OF THE INVENTION

The present invention involves the important discovery that ultrasonic energy applied to contact lenses in a specific power and frequency range operates to remove soil and debris from the lens surfaces within a short time after the energy is applied. This means that if the temperature of the solution into which the lenses are immersed for the application of ultrasonic energy is maintained at levels which do not cause protein denaturation until after mechanical removal of the soil from the lens surfaces has occurred, disinfection by the synergistic effection of elevated temperature and ultrasound can proceed without any occurrence of substantial protein denaturation.

The present invention provides a process for cleaning and disinfecting contact lenses in a single unit operation. The soiled contact lenses are submerged in a bath of a biocompatible, cavitation-supporting solution at ambient temperature. Ultrasonic energy is transmitted through the solution at a frequency of between 62 and 72 kHz and an intensity of between 0.8 and 2.0 watts per ml. to produce cavitation therein. Substantially all of the soil is dislodged from the lens before the combined elapsed time and temperature conditions within the solution produce any substantial protein denaturation on the lens. The transmission of ultrasonic energy through the solution is continued so that the total elapsed exposure time of the bath to the ultrasonic energy is sufficient to effect disinfection of the lenses without requiring the temperature of the bath to rise above approximately 65° C.

The use of the ultrasonic energy cleaning process eliminates the potential for tearing or otherwise damaging the lens that is present in manual cleaning processes. In addition, due to the synergistic effect of the ultrasonic energy and the temperature of the bath, the lens can be disinfected at a lower temperature than would otherwise be required. Therefore, the lenses can be cleaned and disinfected without the danger of degrading the lens material. Further, the relatively low temperature operation of the process of the present invention poses no risk of the user burning his fingers when removing lenses from the cleaning/disinfection unit.

DETAILED DESCRIPTION OF THE PREFERRED EMBODIMENTS

The present invention is directed to a process for cleaning and disinfecting a contact lens in a single-unit operation.

The soiled contact lenses are placed in a container and immersed in a biocompatible, cavitation-supporting saline solution bath at ambient temperature. Any solution, including both preserved and unpreserved salines, that is suitable for cleaning, disinfecting or storing contact lenses is suitable for use in the present invention. Ultrasonic energy is transmitted through the solution at a frequency of between 62 and 72 kHz and an intensity of between 0.8 and 2.0 watts per ml. The cavitation caused by the ultrasonic energy as it is transmitted through the solution dislodges essentially all of the soil from the lens within 90 seconds and before the temperature of the solution reaches 33° C. Thus, the lenses are substantially cleaned before the combined elapsed time and temperature conditions within the solution produce any substantial protein denaturation on the lens.

The relationships between the temperature and cleaning efficacy and the elapsed time were determined according to the following examples:

EXAMPLE 1

Figure 1:
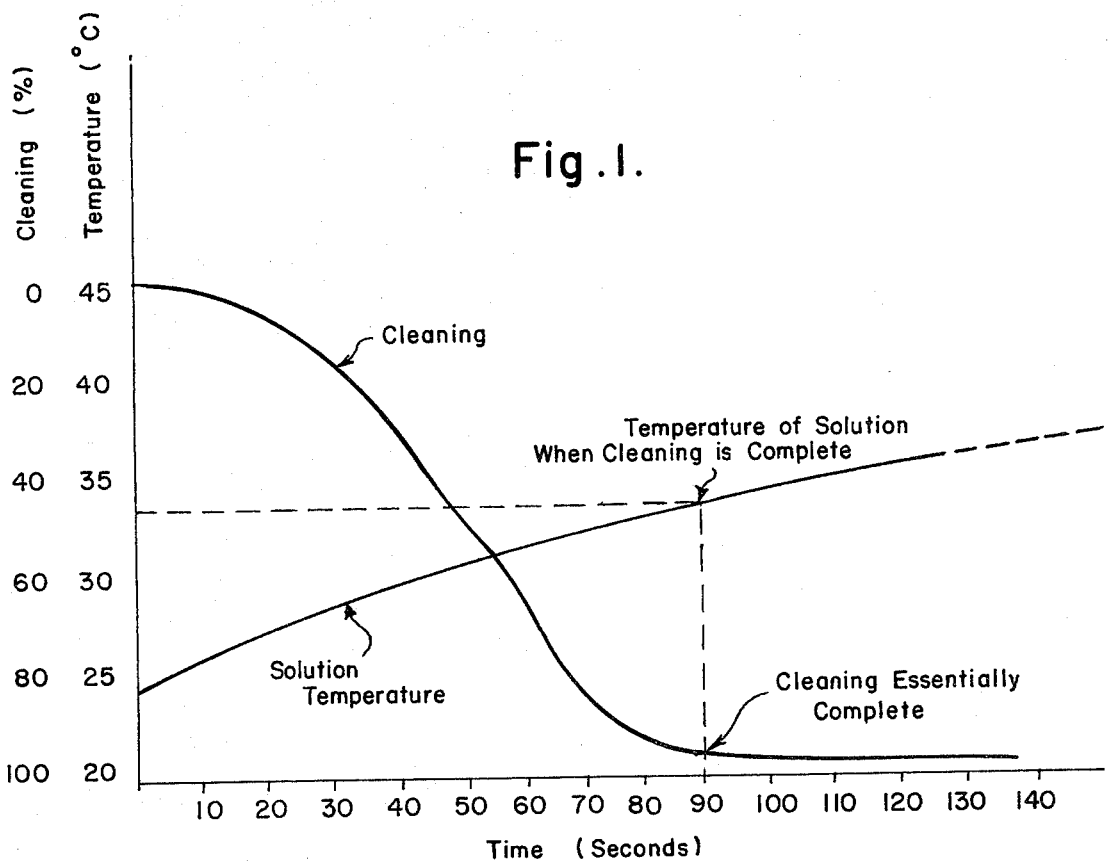
FIG. 1 is a plot of the temperature of the saline solution bath and the cleaning efficacy of the process versus time during the cleaning portion of the process of the invention.

A solution cup of an ultrasonic cleaning/disinfection device was filled with six (6) ml. of isotonic saline solution at ambient (room) temperature. A lens-holding cover with a small hole in the top was placed on the solution cup and a thermocouple was put through the hole and allowed to contact the solution. The thermocouple was connected to a direct reading potentiometric temperature recorder. Thus the solution temperature was recorded as ultrasonic energy was transmitted through the solution at a frequency of between 62 and 72 kHz and an intensity of between 0.8 and 2.0 watts per ml. A summary of the temperature as a function of time is shown in Table 1 and FIG. 1.

TABLE I

| SOLUTION TEMPERATURE | |
|---|---|
| TIME (Seconds) | TEMPERATURE (°C.) |
| 10 | 24 |
| 20 | 25 |
| 30 | 26 |
| 60 | 27.5 |
| 80 | 30 |
| 100 | 32 |
| 120 | 33.5 |

In order to illustrate the ability of the process to clean contact lenses after normal use, the soft contact lenses were coated with lysozyme. Lysozyme is a protein commonly found in deposits on soiled contact lenses because it is a component of natural secretions from the human eye. The lenses were dipped in egg white, a source of lysozyme, and allowed to dry for five (5) minutes. The dried coated lens was then placed in a 10 mm square spectrophotometric cell which has been filled with an isotonic saline solution and oriented in the cell so that the beam of light from the spectrophotometer would pass through the lens. A clean lens of the same characteristics was placed in a reference cell and arranged in the same manner.

An ultraviolet spectrum of between 190 nm and 400 nm was recorded with the cell containing the "clean" lens in the reference position and the lens coated with lysozyme in the sample position. A single absorption maximum was recorded at approximately 280 nm. The same procedure was followed with a lens which had been used for six (6) months. The lens had been disinfected during use by a thermal disinfection procedure which had ultimately caused protein from the eye to deposit on the lens. Again, a single absorption maximum was recorded at approximately 280 nm.

Therefore, the results of tests involving the use of contact lenses coated with egg white give a good indication of what occurs with lenses which have been soiled during use.

In order to determine the ultrasonic cleaning as a function of time several lenses were dipped into egg white and allowed to dry for approximately five (5) minutes. An ultraviolet spectrum was recorded for each lens as described above. An absorption maxima of approximately 280 nm was recorded. The lenses were then individually placed into the ultrasonic cleaning/disinfection device described above and the device was operated for times varying from ten seconds to two minutes. Ultrasonic energy was transmitted through the solution at the same frequency and intensity as it was during the procedure in which the temperature of the solution was recorded. As each time of operation was recorded, the lens was removed from the ultrasonic device, the ultraviolet spectrum was recorded and the absorbance was noted. The percentage difference from the absorbance of the dirty lens and the absorbance of the same lens which had been subjected to ultrasonic cleaning was calculated and a summary of results appears in Table II. A plot of the cleaning efficacy appears superimposed on the temperature plot in FIG. 1.

TABLE II

| CLEANING EFFICACY | |
|---|---|
| TIME (Seconds) | CLEANING (%) |
| 10 | 1.0 |
| 20 | 2.1 |
| 30 | 10.0 |
| 60 | 68.9 |
| 80 | 96.5 |
| 100 | 97.4 |
| 120 | 99.0 |

It may be seen from Example 1 that cleaning is essentially complete while the temperature of the solution remains below about 33° C., well below the temperature at which protein denaturation occurs.

According to the present invention, ultrasonic energy is transmitted continuously through the solution until the lenses have been disinfected. As shown in Example 1, the application of ultrasonic energy to the solution causes an increase in temperature. However, because of the synergistic effect between the ultrasonic energy and the temperature of the solution, the lenses are essentially disinfected within a time period of about 20 minutes. And by employing the preferred values of frequency and intensity indicated above, the solution temperature does not exceed about 65° C. Thus, the lenses are disinfected at a temperature well before there is a danger of damage to the lens material.

The relationships between the temperature and disinfecting efficacy and the elapsed time were determined according to the following example:

EXAMPLE 2

In order to determine the efficacy of disinfection, three representative microorganisms were chosen; *P. aeruginosa*, commonly associated with eye infections, *S. epidermidis*, most commonly found on the skin; *C. albicans*, associated with common infections. Additionally, these three (3) organisms are representative of Gram-negative, Gram-positive and yeast organisms. These microorganisms, therefore, generally represent the classes of pathogens which would normally be encountered by the average contact lens wearer. Suspensions of the test populations were prepared according to standard laboratory techniques.

A solution cup of an ultrasonic cleaning/disinfection device was filled with six (6) ml. of either unpreserved or preserved saline solution. The unpreserved saline contained 0.9% NaCl and purified water. The preserved saline solution contained 0.9% NaCl, 0.001% Thimerosal, 0.1% disodium edetate and water with a borate buffer. Each saline solution was then inoculated with approximately a $10^4$ to $10^6$ population (CFU) of one of the three organisms. Ultrasonic energy was transmitted through the inoculated solution at a frequency of between 62 and 72 kHz and an intensity of between 0.8 and 2.0 watts per ml. until the temperature of the solution reached about 65° C., a time period of about 20 minutes, after which time an aliquot of the solution was removed and spread plated on the surface of trypticase soy agar. This procedure was repeated for each of the microorganisms in both preserved and unpreserved saline solutions.

All plates were incubated at 37° C. for 48 hours at which time the number of colonies, if any, were counted. The results appear in Table III.

TABLE III

| DISINFECTION EFFICACY | | | |
|---|---|---|---|
| Organism | Solution | Initial Population (CFU) | Final Population (CFU) |
| P. aeruginosa | Unpreserved | $3.1 \times 10^4$ | 0 |
| P. aeruginosa | Preserved | $3.1 \times 10^4$ | 0 |
| S. epidermidis | Unpreserved | $3.0 \times 10^4$ | 0 |
| S. epidermidis | Preserved | $3.0 \times 10^4$ | 0 |
| C. albicans | Unpreserved | $4.5 \times 10^6$ | 0 |
| C. albicans | Preserved | $4.5 \times 10^6$ | 0 |

Figure 2:
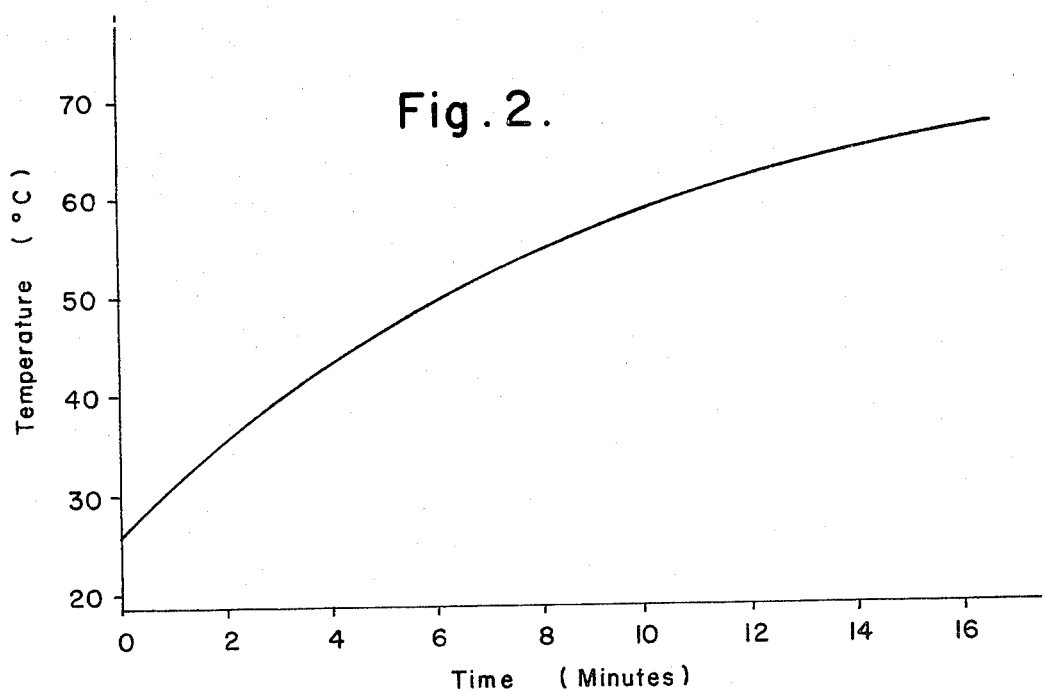
FIG. 2 is a plot of the temperature of the saline solution bath versus time during the process of the present invention.

It can be seen from an analysis of Table III that the procedure adequately disinfected the solutions. The time-temperature plot shown in FIG. 2 was determined in the same way as described in Example 1. It can be seen from an analysis of FIG. 2 that the temperature does not rise above about 65° C. during the twenty minute cleaning and disinfection cycle. Thus the contact lenses are cleaned and disinfected at a temperature which is not high enough to damage the lens material.

EXAMPLE 3

Figure 3:
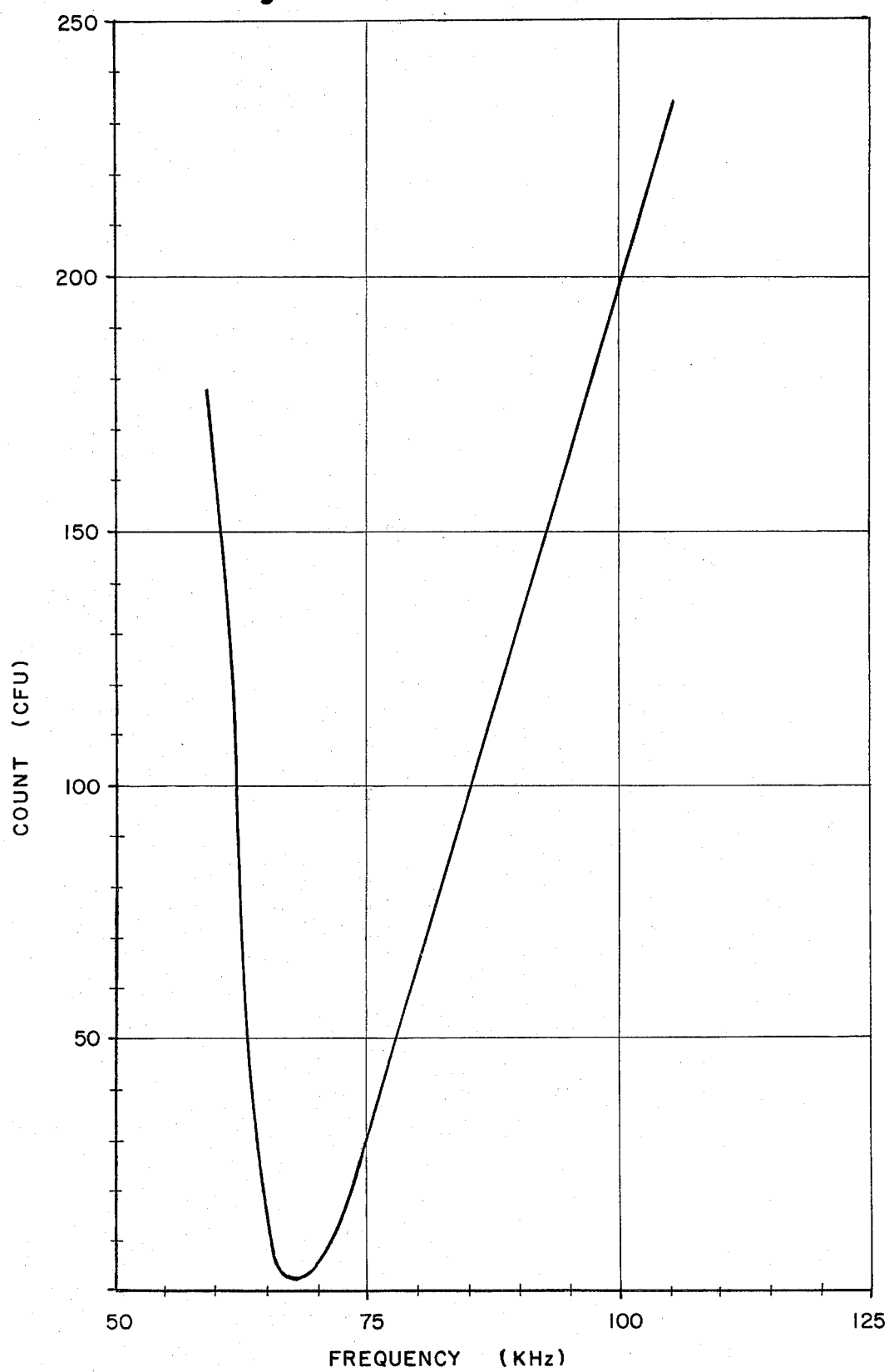
FIG. 3 is a plot of the frequency of the ultrasonic energy versus microbiological growth at a power intensity of 1 watt per ml.

In order to determine the critical range of the frequency of the ultrasonic energy necessary to effect cleaning and disinfection according to the present invention, six (6) ml. samples of unpreserved saline solution were inoculated with approximately a $10^4$ to $10^6$ population (CFU) of either *P. aeruginosa, S. epidermidis* or *C. albicans*. The solution samples were exposed to ultrasonic energy at a frequency of 58, 66, 73 or 105 kHz for a time period of 5, 10 or 20 minutes at an intensity of 1.0 watt per ml. of solution. After the exposure to ultrasonic energy, an aliquot of the solution was removed and spread plated on the surface of trypticase soy agar. The plates were incubated at 37° C. for 48 hours at which time the number of colonies, if any, were counted. The results appear in Table IV. FIG. 3 shows a plot of the relationship between the frequency and the microbiological growth after a 20 minute exposure to the ultrasonic energy.

TABLE IV

| FREQUENCY VS. MICROBIOLOGICAL GROWTH | | | |
| --- | --- | --- | --- |
| | Average Count (CFU) | | |
| Frequency | 5 Min. | 10 Min. | 20 Min. |
| 58 | 170 | 150 | 100 |
| 66 | 3 | 0 | 0 |
| 73 | 7 | 0 | 0 |
| 105 | 232 | 151 | 150 |

It can be seen from an analysis of Table IV and FIG. 3 that ultrasonic energy applied to a contaminated solution at a frequency of between 62 and 72 kHz and an intensity of between 0.8 and 2.0 watts per ml. will disinfect the solution in a time period of not longer than twenty minutes.

What is claimed is:

1. A process for cleaning and disinfecting a soiled contact lens in a single unit operation comprising the steps of:

immersing said lens in a cavitation-supporting, saline solution, said solution being at ambient temperature;

subjecting said lens to ultrasonic energy transmitted through said solution at a frequency in the range of 62 to 72 kHz and an intensity in the range of 0.8 to 2.0 watts per ml. of solution present, said ultrasonic energy producing cavitation in said solution and dislodging substantially all of said soil from said lens before the combined elapsed time and temperature conditions within said solution produce any substantial protein denaturation on said lens; and continuing to transmit said ultrasonic energy through said solution at said frequency and intensity ranges to produce a temperature in said solution not to exceed about 65° C. but sufficient for a total elapsed period of said ultrasonic energy transmission, not to exceed about 20 minutes, to effect disinfection of said lens.

2. A process as recited in claim 1 in which substantially all of said soil is dislodged from said lens within about 90 seconds and before the temperature of said solution reaches about 33° C.

* * * * *